(12) United States Patent
Mukhopadhyay et al.

(10) Patent No.: US 7,189,884 B2
(45) Date of Patent: Mar. 13, 2007

(54) PROCESSES FOR SYNTHESIS OF TETRAFLUOROPROPENE

(75) Inventors: Sudip Mukhopadhyay, Buffalo, NY (US); Haridasan K. Nair, Williamsville, NY (US); HsuehSung Tung, Getzville, NY (US); Michael Van Der Puy, Amherst, NY (US)

(73) Assignee: Honeywell International, Morristown, NJ (US)

( * ) Notice: Subject to any disclaimer, the term of this patent is extended or adjusted under 35 U.S.C. 154(b) by 0 days.

(21) Appl. No.: 11/118,530

(22) Filed: Apr. 29, 2005

(65) Prior Publication Data

US 2006/0030744 A1    Feb. 9, 2006

Related U.S. Application Data

(60) Provisional application No. 60/567,428, filed on Apr. 29, 2004.

(51) Int. Cl.
*C07C 21/18* (2006.01)

(52) U.S. Cl. .................................... 570/160

(58) Field of Classification Search .............. 570/153, 570/160
See application file for complete search history.

(56) References Cited

U.S. PATENT DOCUMENTS

| | | | |
|---|---|---|---|
| 6,369,284 | B1 | 4/1960 | Nappa et al. |
| 2,996,555 | A | 8/1961 | Rausch et al. |
| 3,472,826 | A | 10/1969 | Potts et al. |
| 3,659,023 | A | 4/1972 | Regan |
| 4,650,914 | A | 3/1987 | Woodard et al. |
| 4,798,818 | A | 1/1989 | Balzer et al. |
| 4,900,874 | A | 2/1990 | Ihara et al. |
| 5,532,419 | A | 7/1996 | Van Der Puy et al. |
| 5,545,777 | A | 8/1996 | Morikawa et al. |
| 5,574,192 | A | 11/1996 | Van Der Puy et al. |
| 5,679,875 | A | 10/1997 | Aoyama et al. |
| 5,986,151 | A | 11/1999 | Van Der Puy et al. |
| 6,111,150 | A * | 8/2000 | Sakyu et al. ............. 570/167 |
| 6,124,510 | A | 9/2000 | Elsheikh et al. |
| 6,548,719 | B1 * | 4/2003 | Nair et al. .............. 570/157 |
| 6,809,226 | B1 | 10/2004 | Pennetreau et al. |
| 6,958,424 | B1 * | 10/2005 | Nair et al. .............. 570/261 |
| 2005/0020862 | A1 | 1/2005 | Tung et al. |
| 2005/0080302 | A1 | 4/2005 | Baker et al. |
| 2005/0090698 | A1 | 4/2005 | Merkel et al. |
| 2005/0171391 | A1 | 8/2005 | Janssens et al. |

FOREIGN PATENT DOCUMENTS

| | | |
|---|---|---|
| EP | 0522639 | 1/1993 |
| JP | 11140002 | 5/1999 |
| JP | 2000169404 | 6/2000 |
| WO | WO 9504021 | 2/1995 |
| WO | WO/96/01797 A | 1/1996 |
| WO | WO2005/042451 A | 5/2005 |

OTHER PUBLICATIONS

U.S. Appl. No. 10/694,273, filed Oct. 27, 2003, Singh et al.
Zhuranl Organicheskol Khimii, 28(4), 672-80, (1982).

* cited by examiner

*Primary Examiner*—Thurman K. Page
*Assistant Examiner*—Kellette Gale
(74) *Attorney, Agent, or Firm*—Colleen D. Szuch

(57) ABSTRACT

Disclosed in one embodiment is a process for the synthesis of 1,3,3,3-tetrafluoropropene that comprises (a) reacting a compound of formula (I) $X^1X^2$ with a compound of formula (II) $CF_3CH=CH_2$ to produce a reaction product comprising a compound of formula (III) $CF_3CHX^1CH_2X^2$, wherein $X^1$ and $X^2$ are each independently selected from the group consisting of hydrogen, chlorine, bromine and iodine, provided that $X^1$ and $X^2$ are not both hydrogen; (b) when $X^2$ in formula (III) is not fluorine, fluorinating the compound of formula (III) to produce a reaction product comprising a compound of formula (III) wherein $X^1$ is as described above and $X^2$ is fluorine; and (c) exposing said compound of formula (III) to reaction conditions effective to convert said compound to 1,3,3,3-tetrafluoropropene.

24 Claims, No Drawings

PROCESSES FOR SYNTHESIS OF TETRAFLUOROPROPENE

FIELD OF THE INVENTION

The present invention relates to methods for the preparation of tetrafluorinated propene. More specifically, this invention concerns processes for the preparation of 1,3,3,3-tetrafluoropropene, $CF_3CH=CHF$, (HFO-1234 ze).

BACKGROUND OF THE INVENTION

Tetrafluorpropenes are known to be useful as monomers in the preparation of various homopolymers and copolymers. For example, U.S. Pat. No. 3,472,826 describes tetrafluorpropene as a comonomer in the production of polyethylene. U.S. patent application Ser. No. 10/694,273, which is assigned to the assignee of the present invention, discloses the use of $CF_3CH=CFH$ as a refrigerant with low global warming potential and also as a blowing agent for use in connection with the formation of various types of foams. In addition, $CF_3CH=CFH$ can also be functionalized to variety of compounds useful as intermediates for making industrial chemicals.

Several methods of preparing tetrafluoropropene compounds are known. For example, U.S. Pat. No. 6,548,719 B1 describes generally the production of a wide range of fluoroolefins by dehydrohalogenating, in the presence of a phase transfer catalyst, a compound of formula $CF_3C(R^1{}_aR^2{}_b)C(R^3{}_cR^4{}_d)$ with at least one alkali metal hydroxide, where the R substituents are as defined in the patent, provided that at there is at least one hydrogen and one halogen on adjacent carbon atoms. This patent, while disclosing a process that is efficient and useful for the preparation of numerous tetrafluoropropenes, it does not disclose a process specifically for the preparation of 1,3,3,3-tetrafluoropropene.

The preparation of 1,3,3,3-tetrafluoropropene is specifically disclosed in U.S. Pat. No. 5,986,151. This patent discloses a process comprising catalytic dehydrofluorination of CF3CH2CF2H in the gas phase to afford $CF_3CH=CHF$. The preparation of 1,3,3,3-tetrafluoropropene is also disclosed in U.S. Pat. No. 6,124,510. This patent also discloses a process comprising catalytic dehydrofluorination of $CF_3CH_2CF_2H$ in the gas phase. Each of these patents has the disadvantage of being limited by the requirement of isolating 1,1,1,3,3-pentafluoropropane ("245fa") as a starting reactant, which may be undesirable for reasons of cost, availability, and/or otherwise.

SUMMARY OF THE INVENTION

Applicants have discovered a process for the synthesis of 1,3,3,3-tetrafluoropropene that overcomes at least the deficiencies of the prior art noted above.

The processes of the present invention in accordance with one embodiment generally comprise: (a) reacting a compound of formula (I) $X^1X^2$ with a compound of formula (II) $CF_3CH=CH_2$ to produce a reaction product comprising a compound of formula (III) $CX^2{}_3CHX^1CH_2X^2$, wherein $X^1$ and $X^2$ are each independently selected from the group consisting of hydrogen, chlorine, bromine, fluorine and iodine, provided that $X^1$ and $X^2$ are not both hydrogen; (b) when $X^2$ in formula (III) is not fluorine, fluorinating the compound of formula (III) to produce a reaction product comprising a compound of formula (III) $CX^2{}_3CHX^1CH_2X^2$ wherein $X^1$ is as described above and $X^2$ is fluorine; and (c) exposing said compound to reaction conditions effective to convert said compound of formula (III) to 1,3,3,3-tetrafluoropropene. For the purposes of convenience but not by way of limitation, the processes in accordance with this embodiment are sometimes referred to herein as "the hydrohaolgen addition process."

The processes of the present invention according to another embodiment generally comprise: (a) reacting chlorine with a compound of formula (I) $CH_3CH=CH_2$ to produce a reaction product comprising a compound of formula (II) $CCl_3CHClCH_2Cl$; (b) fluorinating the compound of formula (II) to produce a reaction product comprising a compound of formula (III) $CF_3CHClCH_2F$; and (c) exposing said compound of said formula (III) to reaction conditions effective to convert said compound to 1,3,3,3-tetrafluoropropene. For the purposes of convenience but not by way of limitation, the processes in accordance with this embodiment are sometimes referred to herein as "the chlorination process" since that is the first step in the preferred forms of this embodiment of the process.

The present invention is thus directed to processes for the production of $CF_3CH=CFH$ which are amenable to scale up from readily available and relatively inexpensive starting materials.

DETAILED DESCRIPTION OF PREFERRED EMBODIMENTS

The present invention is directed to methods for the production of both the cis- and trans- isomers of 1,3,3,3 tetrafluoro-2-propene, $CF3CH=CHF$ ("HFC-1234 ze").

For the purposes of convenience, but not by way of limitation, the hydrohalogen addition processes and the chlorination processes will be described separately below.

Hydrohalogen Addition Process

The step of reacting a compound of formula (I) with a compound of formula (II) is amenable to a large number of specific processing condition and steps in accordance with the teachings contained herein, and all such variations are within the broad scope of the present invention. For example, the reaction step may comprise a liquid-phase or a gas phase addition reaction, either catalyzed or uncatalyzed, although catalyzed reactions are generally preferred. For embodiments in which $X^1$ and $X^2$ in formula (I) are each selected from F, Cl, Br, and I, provided that $X^1$ and $X^2$ are not the same, such as when the compound is ClF, then it is preferred that the reaction step comprises exposing the reactants, preferably at a temperature of from about 0° C. to about 100° C., in the presence of a catalyst, preferably an oxide of a group 6 metal, for example $V_2O_5$. For embodiments in which $X^1$ and $X^2$ in formula (I) are the same and are selected from F, Cl, Br, and I, such as when the compound is $Br_2$, then it is preferred that the reaction step (a) comprises exposing the reactants, preferably at a temperature of from about −10° C. to about 50° C. in the presence of a solvent. A wide variety of solvents may be used, such as acetic acid, carbontetrachloride, chloroform, and dichloromethane.

In embodiments in which the reaction step (a) produces a compound of formula (III) wherein $X^2$ in is not fluorine, as would be the case when the formula (II) is $Br_2$, then the resulting compound is subjected to a fluorination. It is contemplated that numerous variations of fluorination conditions are effective for the purposes of the present invention, and all such conditions are within the broad scope of the invention. It is contemplated that fluorination can take place in either the gas or the liquid phase, although gas phase fluorination is generally preferred. For gas phase fluorination, it is generally preferred to utilize a catalyzed, preferably a Cr-oxide ($Cr_2O_3$) catalyzed, gas-phase fluorination at a temperature of from about 250° C. to about 500° C. in the presence HF, preferably anhydrous HF gas. In certain preferred embodiments, a flow reactor is used for the fluorination reaction. The fluorination reaction generally produces a reaction product comprising $CF_3CHX^1CH_2F$, where $X^1$ is preferably not F.

In highly preferred embodiments, the fluorination reaction occurs substantially simultaneously with the step (a) reaction, for example conducting the step (a) reaction in the presence of hydrogen fluoride and under the appropriate conditions, such as disclosed in *Zhuranl Organicheskoi Khimii*, 28(4),672–80, (1982), which is incorporated herein by reference.

It is contemplated that numerous and varied reaction conditions other than the preferred conditions specifically disclosed herein can be utilized with good effect for the reaction step (a) in view of the teachings contained herein.

After the reaction step (a) or after the fluorination step (b) when it is present, the invention requires exposing the compound of formula (III) $CF_3CHX^1CH_2F$ to reaction conditions effective to produce a reaction product comprising 1,3,3,3-tetrafluoropropene. In preferred embodiments, the exposing step comprises dehydrohalogenating the compound of formula (III), in the gas and/or liquid phase. Although it is contemplated that numerous dehydrohalogenation steps can be utilized with good effect in accordance with the teachings contained herein, it is preferred in certain embodiments that the dehydrohalogentaion step comprises contacting the compound of formula (III) with a catalyst at a relatively elevated temperature for a time sufficient to convert the compound to 1,3,3,3-tetrafluoropropene. For dehyrdobromination, it is generally preferred that the compound of formula (III) is reacted in aqueous KOH in the presence of a catalyst. Certain dehydrohalogenation reactions comprise introducing a stream containing the compound of formula (III) into a reactor containing catalyst, preferably a bed of iron-based catalyst, more preferably $FeCl_3$, maintained at temperature of from about 200° C. to about 400° C. and under conditions to produce a contact time of from about 2 seconds to about 30 seconds. Preferably the reaction pressure is maintained at a pressure of from about 0 psig to about 200 psig. The exposing step may also be conducted in accordance with the teachings of U.S. Pat. No. 6,548,719 B1, which is assigned to the assignee of the present invention and which is incorporated herein by reference. Gas phase dehydrofluorination with an appropriate catalyst and at elevated temperature can also be performed in accordance with the procedures as described in U.S. Pat. No. 5,986,151, which is also incorporated hererin by reference.

The exposing step preferably produces a reaction product stream which comprises 1,3,3,3-tetrafluoropropene, more preferably comprises a major proportion of 1,3,3,3-tetrafluoropropene, and even more preferably comprises at least about 45% 1,3,3,3-tetrafluoropropene. The yield of 1,3,3,3-tetrafluoropropene based on the amount of compound (III) in the exposing step is preferably at least about 60% (mol).

Any by-products contained in the reaction product stream can be removed to the extent desired by known means, such as distillation etc.

One particular embodiment of the present invention involves the reaction steps set forth as Scheme 1, below:

Scheme 1

Applicants note that the embodiment of the invention depicted by Scheme 1 above may, in certain cases, produce as a by product a compound of formula $CF_3CHFCH2X^1$, where $X^1$ is a halogen other than fluorine, and that in certain preferred embodiments it may be preferred to carry out the further step of reacting such a compound, preferably by dehydrohaolgenation, to produce a desirable fluoroolefin of the present invention, namely, CF3CF=CH2 (HFO-1234yf). For example, in the scheme described above, the first reaction in certain embodiments may result in the producton of produce CF3CHFCH2Br, and that this can be dehydrobrominated to produce HFO-12324yf.

Another particular embodiment of the present invention involves IF addition across the double bond and subsequent dehalogentaion to give $CF_3CH=CFH$, as depicted in Scheme 2 below:

Scheme 2

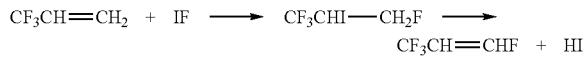

In a manner similar to that described above in connection with Scheme 1, applicants note that the embodiment of the invention depicted by Scheme 2 above may, in certain cases, produce as a by product a compound of formula $CF_3CHFCH_2I$ and that in certain preferred embodiments it may be preferred to carry out the further step of reacting such a compound, preferably by dehyrdoionization, to produce a desirable fluoroolefin of the present invention, namely, CF3CF=CH2 (HFO-1234yf).

Chlorination Processes

The reacting step (a) according to this embodiment is a chlorination step which, in the broad aspects, is amenable to a large number of specific processing condition and steps in accordance with the teachings contained herein, and all such variations are within the broad scope of the present invention. It is particularly preferred, however, that the reaction step (a) comprise photochlorination. Thus, the preferred reaction step (a) comprises exposing the reactants, preferably in a liquid phase, to ultraviolet radiation, preferably in the range of from about 200 to about 400 nm, neat in the presence of a chorination catalyst, preferably an Au/TiO$_2$ catalyst. The reactants are preferably carried in a solvent, more preferably a chlorinated solvent such as $CCl_4$. The reaction is preferably carried out a temperature of from about 0° C. to about 300° C., and even more preferably from about 0° C. to about 300° C. for a time of from about 0.5 hours to about 70 hours, more preferably from about 0.5 hours to about 48 hours. The reaction product, which comprises a compound of formula (II), may then optionally be subject to one or more separation steps, such as distillation, to remove unwanted byproducts and produce a stream relatively concentrated in compounds of the formula (II).

The compound of formula (II) from the reaction step (a) is, after the optional separation step(s), subjected to fluorination. It is contemplated that numerous variations of fluorination conditions are effective for the purposes of the present invention, and all such conditions are within the broad scope of the invention. It is contemplated that fluorination can take place in either the gas or the liquid phase, although gas phase fluorination is generally preferred. For gas phase fluorination, it is generally preferred to utilize a catalyzed, preferably a Cr-oxide ($Cr_2O_3$) catalyzed, gas-phase fluorination at a temperature of from about 250° C. to about 500° C., and even more preferably from about 250° C. to about 400° C. in the presence HF, preferably anhydrous HF gas. In certain preferred embodiments, a flow reactor is used for the fluorination reaction, and the reaction is preferably conducted under conditions to produce a contact time of from about 1 seconds to about 50 seconds, and even more preferably from about 5 seconds to about 50 seconds. The fluorination reaction generally produces a reaction product comprising a compound of the formula (III) $CF_3CHClCH_2F$.

It will be appreciated that in certain preferred embodiments, the fluorination reaction may occur substantially simultaneously with the step (a) reaction, for example conducting the step (a) reaction in the presence of hydrogen fluoride and under the appropriate conditions.

After the reaction step (a) and the fluorination step (b), this embodiment of the present invention preferably includes exposing the compound of formula (III) CF3CHClCH2F to reaction conditions effective to produce a reaction product comprising 1,3,3,3-tetrafluoropropene. In preferred embodiments, the exposing step comprises dehydrochlorinating the compound of formula (III), in the gas and/or liquid phase. Although it is contemplated that numerous dehydrochlorination steps can be utilized with good effect in accordance with the teachings contained herein, it is preferred in certain embodiments that the dehydrochlorination step comprises contacting the compound of formula (III) with a catalyst at a relatively elevated temperature for a time sufficient to convert the compound to 1,3,3,3-tetrafluoropropene. Preferably the dehydrochlorination reaction comprises introducing a stream containing the compound of formula (III) into a reactor containing catalyst, preferably a bed of iron-based catalyst, more preferably $FeCl_3$, maintained at temperature of from about 200° C. to about 400° C. and under conditions to produce a contact time of from about 2 seconds to about 50 seconds, and more preferably from about 20 seconds to about 30 seconds. Preferably the reaction pressure is from about 0 psig to about 200 psig. The exposing step may also be conducted in accordance with the teachings of U.S. Pat. No. 6,548,719 B 1, which is assigned to the assignee of the present invention and which is incorporated herein by reference. Gas phase dehydrochlorination with an appropriate catalyst and at elevated temperature can also be performed in accordance with the procedures as described in U.S. Pat. No. 5,986,151, which is also incorporated herein by reference.

The exposing step preferably produces a reaction product stream which comprises 1,3,3,3-tetrafluoropropene, more preferably comprises a major proportion of 1,3,3,3-tetrafluoropropene, and even more preferably comprises at least about 50% by weight of 1,3,3,3-tetrafluoropropene. The yield of 1,3,3,3-tetrafluoropropene based on the amount of compound (III) in the exposing step is preferably at least about 60% (mol).

Any by-products contained in the reaction product streams of any embodiments of the present invention generally can be removed to the extent desired by known means, such as distillation etc.

The following examples are given as specific illustrations of the invention. It should be noted that, however, that the invention is not limited to the specific details set forth in the examples. All isomers (cis and trans) of $CF_3CH=CFH$ are within the scope of the invention.

EXAMPLES

Example 1

Synthesis of $CF_3CH=CHF$ from $Br_2$ and HF (BrF) and $CF_3CH=CH_2$ $CF_3CH=CH_2$ (0.5 mol ) is reacted with $Br_2$ (0.4 mol) and HF (50 mol) in an teflon lined monel autoclave at about −30° C. to −60° C. in the presence of about 0.005 mol of $FeCl_3$ or $SbF_5$ as the catalyst. The reaction time was approximately 10 to 30 mins at that temperature and then 1 h at room temperature. The reaction products are extracted in $CH_2Cl_2$. The major product was $CF_3CHBrCH_2F$ (55%), the byproduct was mainly $CF_3CHBrCH_2Br$ (40%). $CF_3CHBrCH_2F$ was then isolated by distillation which was then dehydrobrominated by passing it over a catalyst bed consisting of about 50 gm of activated carbon at 525° C. with a contact time of about 20 to about 30 seconds to produce a reaction product containing $CF_3CH=CHF$ in a yield of from about 95%.

Example 2

Synthesis of $CF_3CH=CHF$ from IF and $CF_3CH=CH_2$ $CF_3CH=CH_2$ is reacted with IF (formed by the reaction of $I_2$ and $IF_5$ or $I_2$ and HF) in appropriate ratios and under conditions effective to produce $CF_3CHICH_2F$, which is then dehydroiodinated under conditions effective to produce a reaction product containing $CF_3CH=CHF$, preferably in a yield of from about 95%.

Example 3

Synthesis of $CF_3CH=CHF$ from $CH_3CH=CH_2$ and $Cl_2$

About 0.5 mol of $CH_3CH=CH_2$ is reacted with 0.2 mol of $Cl_2$ at 0° C. in a flow reactor under UV (200–400 nm) light in the presence of 1–3% Au/TiO2 catalyst, and $CC_{14}$ is used as a solvent. The reaction is conducted at 0 to 10° C. for about 5 to 20 sec to afford $CCl_3CHClCH_2Cl$. The product thus formed is then isolated and passed through a flow reactor for a contact time for about 5 to 50 seconds at about 250–400° C. in the presence of 5 molar excess of HF over a 50 g ⅛-inch $Cr_2O_3$ catalyst bed to give $CF_3CHClCH_2F$. The $CF_3CHClCH_2F$ was then dehydrochlorinated by passing it over $Cr_2O_3$ catalyst (50 g) at 425–550° C. with a contact time of 25 to 30 seconds to afford $CF_3CH=CFH$. The isolated yield of $CF_3CH=CFH$ ranged from 40–60%.

What is claimed is:

1. A process for the synthesis of 1,3,3,3 tetrafluoropropene comprising:
   a) reacting a compound of formula (I) $X^1X^2$ with a compound of formula (II) $CF_3CH=CH_2$ to produce a reaction product comprising a compound of formula (III) $CF_3CHX^1CH_2X^2$, wherein $X^1$ and $X^2$ are each independently selected from the group consisting of hydrogen, fluorine, chlorine, bromine and iodine, provided that $X^1$ and $X^2$ are not both hydrogen;
   b) when $X^2$ in formula (III) is not fluorine, fluorinating the compound of formula (III) to produce a reaction product comprising a compound of formula (III) wherein $X^1$ is as described above and $X^2$ is fluorine; and c) exposing said compound of formula (III) to reaction conditions effective to convert said compound to 1,3,3,3-tetrafluoropropene.

2. The process of claim 1 wherein $X^1$ and $X^2$ in formula (I) are each selected from F, Cl, Br, and I, and wherein $X^1$ and $X^2$ are not the same.

3. The process of claim 2 wherein said reaction step (a) comprises reacting said compound of formula (I) with said compound of formula (II) at a temperature of from about 0° C. to about 250° C. in the presence of a catalyst.

4. The process of claim 3 wherein said catalyst comprises an oxide of a group 6 metal.

5. The process of claim 4 wherein said catalyst comprises $V_2O_5$.

6. The process of claim 2 where said compound of formula (I) comprises ClF.

7. The process of claim 1 wherein $X^1$ and $X^2$ in formula (I) are each the same and are selected from F, Cl, Br, and I.

8. The process of claim 7 wherein the reaction step (a) comprises reacting said compound of formula (I) with said compound of formula (II) at a temperature of from about −10° C. to about 10° C. in the presence of a solvent.

9. The process of claim 1 wherein said reacting step (a) and said fluorination step (b) occur substantially simultaneously.

10. The process of claim 1 wherein said exposing step comprises dehydrohalogenating the compound of formula (III).

11. The process of claim 10 wherein $X^1$ and $X^2$ in formula (I) are each the same and are selected from F, Cl, Br, and I.

12. The process of claim 11 wherein said dehydrohalogenating step comprises reacting.

13. A process for the synthesis of 1,3,3,3 tetrafluoropropene comprising:

a) reacting chlorine with a compound of formula (I) $CH_3CH\!=\!CH_2$ to produce a reaction product comprising a compound of formula (II) $CCl_3CHClCH_2Cl$;

b) fluorinating the compound of formula (II) to produce a reaction product comprising a compound of formula (III) $CF_3CHClCH_2F$; and c) exposing said compound of formula (III) to reaction conditions effective to convert said compound of formula (III) to 1,3,3,3-tetrafluoropropene.

14. The process of claim 13 wherein said exposing step comprises exposing said formula (III) compound in a reactor to an Fe-based catalyst.

15. The process of claim 13 wherein said exposing step comprises introducing said formula (III) compound into a reactor containing Fe-salt.

16. The process of claim 13 wherein said reacting step a) comprises exposing said chlorine and said formula (I) compound to UV radiation.

17. The process of claim 16 wherein said reaction of step a) is carried out at a temperature of from about 0° C. to about 300° C.

18. The process of claim 16 wherein said reaction step a) is a liquid phase reaction.

19. The process of claim 18 wherein said reaction step a) comprises reacting chlorine and said compound of formula (I) in the presence of a catalyst comprising Au and an oxide of Ti.

20. The process of claim 16 wherein said reaction step a) is a liquid phase reaction and wherein $CCl_4$ is a solvent for said liquid phase reaction.

21. A process for the synthesis of 2,3,3,3 tetrafluoropropene (HFO-1234yf) comprising:

a) reacting one or more compounds of formula (I) $X^1X^2$ with a compound of formula (II) $CF_3CH\!=\!CH_2$ to produce a reaction product comprising a compound of formula (III) $CF_3CHX^1CH_2X^2$, wherein $X^1$ and $X^2$ are each independently selected from the group consisting of hydrogen, fluorine, chlorine, bromine and iodine, provided that $X^1$ and $X^2$ are not both hydrogen and that $X^1$ in formula (III) is fluorine and that $X^2$ in formula (III) is a halogen other than fluorine; and b) exposing said compound of formula (III) to reaction conditions effective to convert said compound to 2,3,3,3-tetrafluoropropene.

22. The process of claim 21 wherein said exposing step b) comprises dehydrohalogenation.

23. A process for the synthesis of 2,3,3,3 tetrafluoropropene (HFO-1234yf) comprising:

a) reacting IF with a compound of formula (II) $CF_3CH\!=\!CH_2$ to produce a reaction product comprising $CF_3CHF\!-\!CH_2I$; and b) exposing said $CF_3CHF\!-\!CH_2I$ to reaction conditions effective to convert said compound to 2,3,3,3-tetrafluoropropene.

24. The process of claim 23 wherein said exposing step b) comprises dehyrdoiodination.

* * * * *